United States Patent [19]
Wu

[11] Patent Number: 4,982,729
[45] Date of Patent: Jan. 8, 1991

[54] RIGID FIBEROPTIC INTUBATING LARYNGOSCOPE

[76] Inventor: Tzu-Lang Wu, 1522 Blackfoot Dr., Fremont, Calif. 94539

[21] Appl. No.: 447,611

[22] Filed: Dec. 8, 1989

Related U.S. Application Data

[63] Continuation-in-part of Ser. No. 308,526, Feb. 10, 1989, abandoned.

[51] Int. Cl.⁵ .............................................. A61B 1/26
[52] U.S. Cl. .................................. 128/11; 128/200.26
[58] Field of Search ...................... 128/3, 4, 10, 11, 17, 128/18, 200.26

[56] References Cited

U.S. PATENT DOCUMENTS

| | | | |
|---|---|---|---|
| 328,619 | 10/1885 | Sperry | 128/17 |
| 2,769,441 | 11/1956 | Abramson | 128/4 |
| 4,294,235 | 10/1981 | Storz | 128/11 |
| 4,306,547 | 12/1981 | Lowell | 128/11 |
| 4,527,553 | 7/1985 | Upsher | 128/11 |

FOREIGN PATENT DOCUMENTS 8902719 4/1989 PCT Int'l Appl. .................. 128/11

Primary Examiner—Edward M. Coven
Assistant Examiner—Mark S. Graham
Attorney, Agent, or Firm—Glen R. Grunewald

[57] ABSTRACT

A laryngoscope comprised of an integral handle and blade wherein the blade is curved to pass over the patient's tongue, the blade also having two fiberoptic bundles for viewing and illuminating the region around the patient's larynx, and a bivalve element that is releasably attachable to the blade to form a passageway for threading an endotracheal tube to the distal end of the blade.

4 Claims, 3 Drawing Sheets

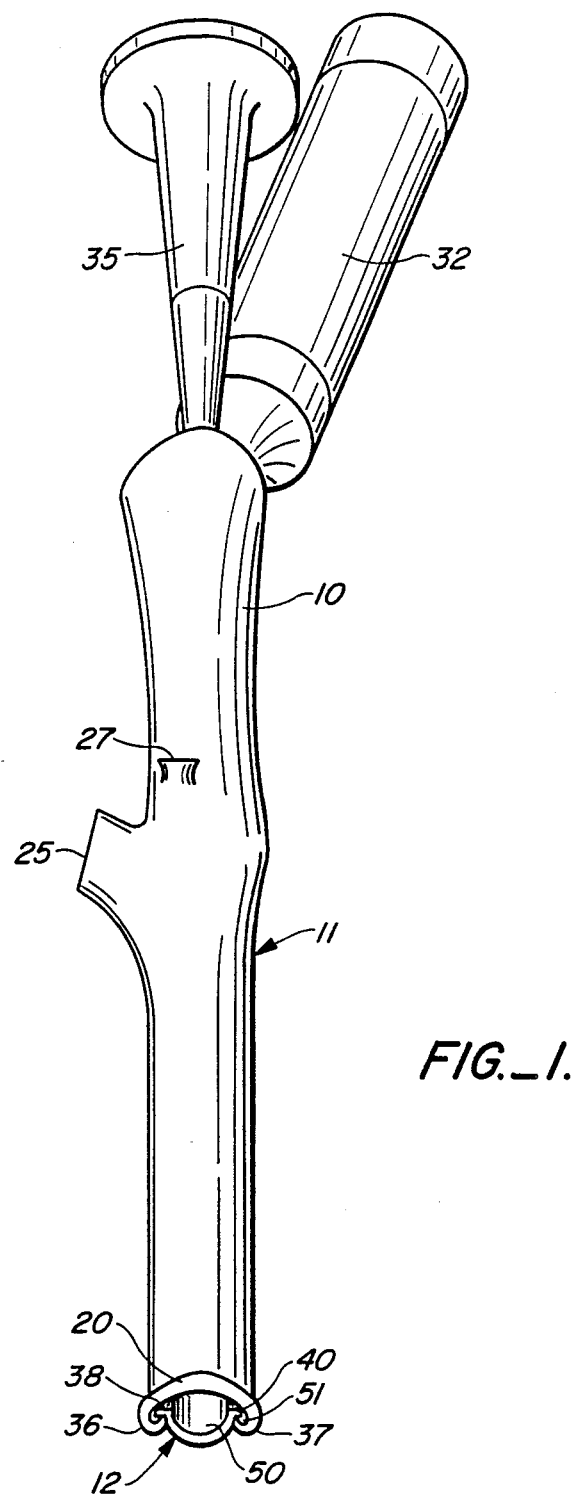
FIG._1.

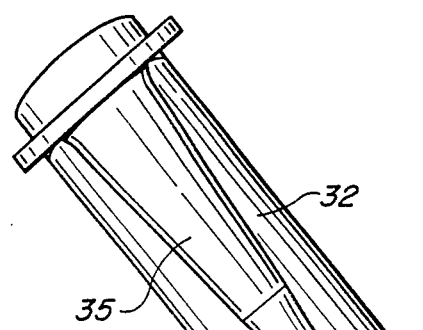
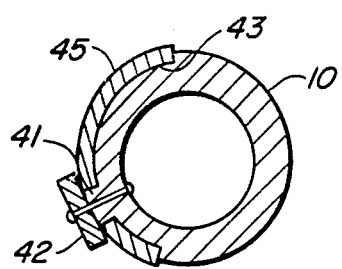
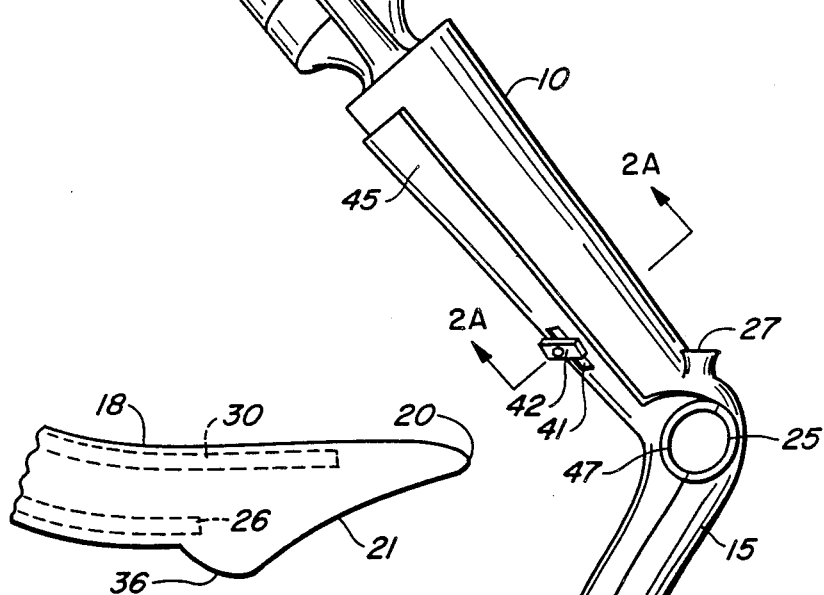
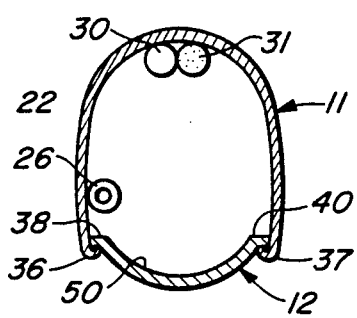
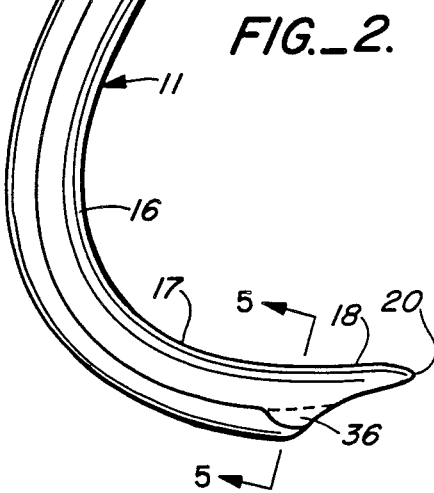
FIG._2A.
FIG._4.
FIG._2.
FIG._5.

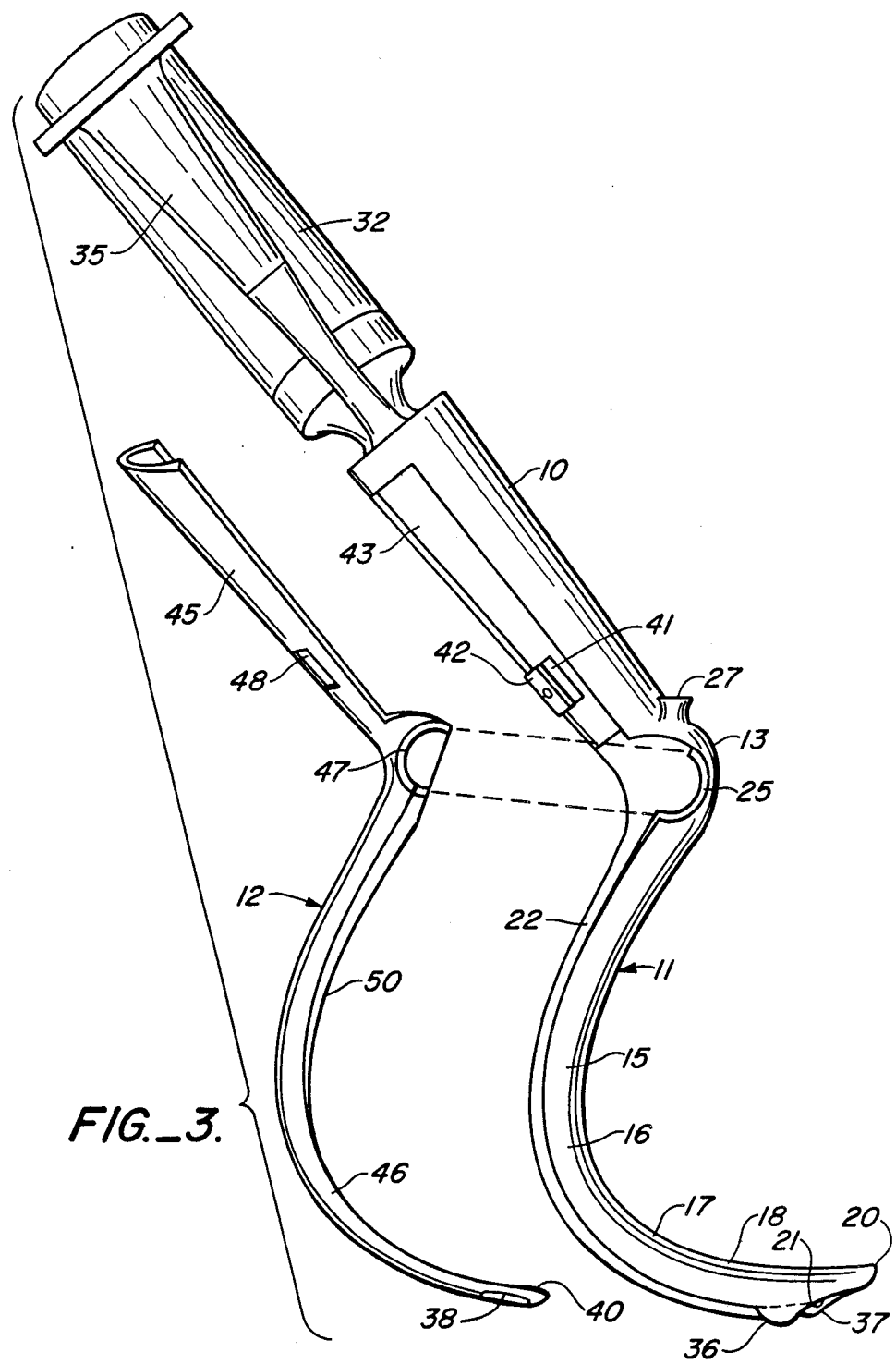
FIG._3.

RIGID FIBEROPTIC INTUBATING LARYNGOSCOPE

CROSS REFERENCE

This application is a continuation-in-part of my copending application Ser. No. 07/308,526, filed Feb. 10, 1989, abandoned and entitled RIGID FIBEROPTIC INTUBATING LARYNGOSCOPE.

FIELD OF THE INVENTION

This invention is in the field of medical instruments, particularly laryngoscopes used to intubate patients.

BACKGROUND ART

A laryngoscope is used by a medical professional for procedures that require access to a patient's larynx. One such procedure is intubating the trachea in order to assist or restore a patient's ability to breath. Intubation is performed during surgery, and the ability to intubate a patient rapidly in an emergency is very important.

A conventional laryngoscope has substantially a straight blade. When using a straight-blade laryngoscope to assist in an intubation procedure a physician must insert the laryngoscope blade so that the upper front teeth, the base of the tongue and the larynx of the patient are in a straight line. Only then can the physician directly see the larynx through which intubation is effected. Many patients have low mobility in the head and neck region while others have anatomical variations that prevent a straight line alignment of the upper front teeth, tongue base and larynx and intubating such patients is very difficult because the larynx cannot be seen.

Laryngoscopes fitted with fiberoptic bundles are known. Such laryngoscopes permit a physician to view the larynx even in difficult alignment situations. However, even when a patient's laryn is visible it is sometimes difficult to align the flexible endotracheal tube with the larynx opening and to insert the flexible tube through the larynx. Sometimes a stylet or forceps must be used to guide the tube and the use of such instruments frequently causes injury to the patient.

DISCLOSURE OF THE INVENTION

This invention is a laryngoscope that overcomes or greatly mitigates the problems with known laryngoscopes. The laryngoscope of this invention includes a blade and a handle. Preferably, the handle is attached to the blade at an angle so that the blade may enter the upper oral cavity with minimal maneuvering of the patient's head and neck. In a preferred embodiment the axis of the handle and the axis of the blade are at an angle of between about 100° and 120°.

The blade includes a substantially straight section that is attached to the handle and the midportion of the blade is shaped as an arc, preferably a circular arc, which in turn is attached to a distal portion of the blade that is straight or substantially straight. The three portions of the blade are integral and are described as three separate portions to facilitate explanation. The curvature of the midportion of the blade avoids the difficult alignment problems because its curved portion conforms to the shape of the patient's anatomy. The laryngoscope of this invention does not require the patient's upper front teeth, tongue base and larynx to be manipulated into a straight line.

The blade is laterally curved to form a groove that runs the length of the blade. The groove opens toward the convex portion of the blade.

The laryngoscope of this invention also includes a bivalve element shaped to correspond with the shape of the blade. The bivalve element includes a longitudinal groove opening toward the concave side of the curved portion. The groove in the blade coacts with a groove in the bivalve element when they are positioned together to form a passageway from the handle to the distal end of the blade. The bivalve element is releasably attachable to the distal end of the blade as well as being releasably attachable to the handle. The passageway formed between the blade and the bivalve element is large enough in diameter to loosely hold an endotracheal tube.

The invention also includes an opening into the passageway between the blade and the bivalve element positioned to permit insertion of the flexible endotracheal tube into the passageway and to slide it through the passageway towards the distal end of the blade.

In the particularly preferred embodiment of the invention the blade is provided with two fiberoptic bundles which run through the blade and terminate at or near its distal end. One bundle is connected at its other end to a source of light which will illuminate the region around the distal end of the blade and the other fiberoptic bundle is connected at its other end to a viewing means so that the illuminated region can be seen by an operator.

In still another embodiment of the invention the blade is provided with an oxygen tube through which oxygen can be supplied to the region around the distal end of the blade.

BRIEF DESCRIPTION OF THE DRAWINGS

FIG. 1 is a front view of a laryngoscope embodying the invention.

FIG. 2 is a left side view of the blade of FIG. 1.

FIG. 2A is a cross section taken along the line 2A—2A of FIG. 2.

FIG. 3 is an exploded left side view of the laryngoscope illustrated in FIG. 1.

FIG. 4 is an enlarged, exploded, perspective view of the distal end of the device.

FIG. 5 is a cross section taken along the line 5—5 of FIG. 2.

BEST MODE FOR CARRYING OUT THE INVENTION

The illustrated laryngoscope includes a handle generally designated 10, a blade generally designated 11, and a bivalve element generally designated 12. The blade and the handle in the illustrated embodiment are a single, integral piece connected together at an angular connection at 13.

The blade 11 includes a substantially straight portion 15 adjacent to the angular connection and an arcuate midportion 16 that is integral with the straight portion and which is also integral with and flows into a substantially straight distal portion 17. The blade terminates in a distal end 18 which is smooth and preferably has an extending point 20 and a rearwardly tapering opening 21. The blade 11 has a transverse curvature providing a groove 22 running the entire length of the blade and opening toward the convex side of the arcuate midportion 16. The angular connection 13 includes a partial opening 25 which coacts with a corresponding partial opening 47 of the bivalve element 12 to form a passageway as will be described in more detail hereinafter. The blade also is provided with an oxygen tube 26 which opens a few centimeters short of the distal end of the blade and is connected to an oxygen feed opening 27 in the handle or in the angular connection 13. The illustrated laryngoscope includes two fiberoptic bundles 30 and 31 which open near the distal end of the blade and run entirely through blade 11 and handle 10. Fiber optic bundles 30 and 31 preferably are spaced about 1.5—2 cm from opening 21. One fiberoptic bundle is functionally connected to light source 32 and the other is functionally connected to eye piece 35. The fiberoptic bundle that is functionally connected to the light source 32 is used by an operator to illuminate the region around distal end 18 while the fiberoptic bundle connected to eye piece 35 is used to view the illuminated region to aid in manipulating the laryngoscope.

As best shown in FIGS. 4 and 5 the distal end 18 of the blade is provided with projecting enlargements 36 and 37 which are employed with cooperating elements on the bivalve element to make an easily releasable interconnection between the blade and the bivalve element. Bivalve flanges 38 and 40 interlock with elements 36 and 37, respectively, when the blade and the bivalve element are held closely together as shown in FIG. 5. A holding member 41 on handle 10 is used to position and interlock with that portion of bivalve element 1 that is in contact with handle 10 when the laryngoscope of this invention is in use.

Bivalve element 12 has portions corresponding in position and shape to handle 10 and blade 11. The portion corresponding to handle 10 is generally designated 45, the portion corresponding to blade 11 is generally shown at 46. The bivalve element includes a partial opening 47 which coincides positionally with partial opening 25 when the projecting enlargements 36 and 37 are engaged with flanges 38 and 40 and when holding member 41 is positioned within opening 48. Holding member 41 may include an interlock means 42 to hold handle portion 45 to handle 10 whereby the positional relationships between the blade and the bivalve element are maintained. A cavity 43 in handle 10 closely fits the shape of portion 45 of the bivalve element to form a secure fit between the entire bivalve element and the blade and handle of the laryngoscope.

FIGS. 1 and 3 illustrate that bivalve element 12 includes a groove 50 opening towards the concave side of the bivalve blade part 46 and when the blade and bivalve element are interlocked in operating position with respect to each other an enclosed passageway is formed between them. The enclosed passageway opens through an opening formed by the relationship between partial opening 25 and partial opening 47 in a manner such that an endotracheal tube may be inserted through that opening, pushed through the passageway formed between blade 11 and bivalve blade part 46 so that it will extend entirely through that passageway and exit through the distal end 18 of the device.

To use the device of this invention flanges 38 and 40 are placed in interlocking relationship within the smooth interior recesses in projecting enlargements 36 and 37 in the distal end of the blade. Only recess 51 can be seen in projecting enlargement 37. Another symmetric element is formed in projecting enlargement 36. With the flanges 38 and 40 so placed the bivalve segment is swung adjacent to corresponding blade and handle elements so that portion 45 enters cavity 43 and holding member 41 protrudes through opening 48. Interlock means 42 may then be turned to secure all elements together to form a unitary structure in the shape of a laryngoscope. The interlocking of the blade, handle and bivalve elements can be accomplished very quickly.

When it is necessary to insert an endotracheal tube the device of this invention may be inserted through a patient's mouth and it may easily be positioned so that distal end 18 is in the immediate vicinity of the larynx because the curvature of blade 11 does not require bending the patient's head and neck to provide a straight-line viewing path over the patient's tongue. The light source 32 may be illuminated and the operator may view the region of the patient's larynx through eye piece 35. The angular connection between handle 10 and blade 11 makes it very easy to insert and manipulate the blade within the patient's mouth and throat. It also places the operator's hand out of alignment with the oral cavity which further improves the ability of the operator to see what he is doing and to manipulate instruments within the oral cavity. When the distal end 18 of the laryngoscope is adjacent the larynx the endotracheal tube may be pushed through the opening formed by partial openings 25 and 47 and easily threaded down the passageway formed by the positional relationship of the blade 11 and the bivalve element 12. The tube will emerge from distal end 18 positioned exactly where it must be thrust through the larynx to intubate the patient. The flexibility of the tube is not a negative factor in intubation when using the device of this invention because only a short length of the tube extends beyond the distal end of the laryngoscope before it enters the larynx opening and that short end is relatively stiff and precisely positioned to penetrate that opening.

When the larynx is intubated, the interlock between holding member 41 and opening 48 is released, bivalve handle portion 45 is swung from handle 10 in a manner to disengage the distal end of the bivalve element from the blade. The bivalve element may then be removed from the patient's oral cavity independently of the blade and the blade may be removed from the patient's oral cavity independently of the endotracheal tube. As a result, the entire laryngoscope may be quickly removed from the patient leaving the endotracheal tube in place inserted through the larynx. The entire operation may be accomplished quickly and with minimum damage to the patient because it is not necessary to manipulate the patient's head and neck to provide alignment for the laryngoscope, it is not necessary to insert the tube by feeling for its proper position in that the area can be seen, it is not necessary to manipulate a flexible tube at the critical area because the tube is held within the rigid laryngoscope and because when the tube is inserted in its desired position all of the apparatus of the laryngoscope may be removed independently and quickly.

The laryngoscope of this invention permits an operator to grasp the handle, to manipulate the blade and look through the eye piece using only one hand, thereby freeing the other hand to use other instruments or to perform other tasks. This is an important feature which is particularly advantageous in emergency situations.

The laryngoscope of this invention may be modified appropriately for other procedures. For example, portions of the bivalve element may be shaped to provide an opening for an endotracheal tube at the midportion of the blade so that intubation through a nasal passage may be effected. In such case, a laryngoscope with the blade and bivalve element appropriately interlocked may be inserted far enough into a patient's oral cavity to insert an endotracheal tube into the passageway formed by the interlocked blade and bivalve element after which the laryngoscope is further inserted into the patient's oral cavity to a position closely adjacent the larynx. Other modifications of the invention may be made without departing from the scope of the claims.

What is claimed is:

1. A laryngoscope comprising:
    a handle;
    a blade connected to said handle, said blade having a substantially straight portion connected to said handle, an arcuate midportion, a substantially straight distal position terminating at a distal end, a first groove running the length of said blade and opening on the convex side of said arcuate midportion;
    a bivalve element having an arcuate portion, a distal end, and substantially straight portions shaped to register with corresponding portions of said blade, a second groove running the length of said arcuate portion, said blade and said bivalve element connectable together with corresponding shaped portions in contact such that said first groove and said second groove form an elongated passageway running substantially from the connection between said blade and said handle to the distal end of said blade;
    first interlocking means located at the distal end of said blade;
    second interlocking means located at the distal end of said bivalve element, said first and second interlocking means being positionable to form a releasable interlock when brought into contact with each other;
    holding means to releasably connect said bivalve element to said handle, and
    an opening into said elongated channel formed between cooperating elements of said blade and said bivalve element.

2. The laryngoscope of claim 1 having two fiberoptic bundles running from said handle through said blade and terminating at said blade distal end, one of said bundles having illuminating means at its handle end and the other of said bundles having viewing means at its handle end.

3. The laryngoscope of claim 1 having an oxygen tube discharging at said blade distal end.

4. The laryngoscope of claim 1 wherein said handle is connected to said blade with the longitudinal axis of said handle at an angle of from about 100° to about 120° with the longitudinal axis of said portion of said blade connected to said handle.

* * * * *